United States Patent [19]

Wenckus

[11] Patent Number: 4,488,821

[45] Date of Patent: * Dec. 18, 1984

[54] METHOD AND MEANS OF RAPIDLY DISTINGUISHING A SIMULATED DIAMOND FROM NATURAL DIAMOND

[75] Inventor: Joseph F. Wenckus, Needham, Mass.

[73] Assignee: Ceres Electronics Corporation, Billerica, Mass.

[*] Notice: The portion of the term of this patent subsequent to Mar. 17, 1998 has been disclaimed.

[21] Appl. No.: 444,212

[22] Filed: Nov. 24, 1982

Related U.S. Application Data

[63] Continuation of Ser. No. 240,126, Mar. 3, 1981, Pat. No. 4,364,677, which is a continuation of Ser. No. 885,502, Apr. 10, 1978, Pat. No. 4,255,962.

[51] Int. Cl.³ ............................................ G01N 25/18
[52] U.S. Cl. ..................................................... 374/44
[58] Field of Search .................. 374/7, 44; 73/75, 154

[56] References Cited

U.S. PATENT DOCUMENTS

| | | | |
|---|---|---|---|
| 2,264,968 | 12/1941 | DeForest | 374/7 |
| 2,362,344 | 11/1944 | Baver et al. | 73/75 |
| 2,951,360 | 9/1960 | Sampson et al. | 374/44 |
| 3,611,786 | 10/1971 | Schorr | 374/44 |
| 3,668,927 | 6/1972 | Howell et al. | 73/154 |

FOREIGN PATENT DOCUMENTS 855658 1/1960 United Kingdom ................ 374/44

OTHER PUBLICATIONS

Lagagette Instrument Company, "Operation and Maintenance for TC-100 Thermal Comparator".

Primary Examiner—Herbert Goldstein
Attorney, Agent, or Firm—Hamilton, Brook, Smith & Reynolds

[57] ABSTRACT

A simulated diamond such as crystalline cubic zirconia, which has optical properties very similar to natural diamond and so is difficult to distinguish optically from natural diamond, is distinguished from natural diamond by measuring its thermal conductivity which is significantly different from the thermal conductivity of natural diamond, by measuring the temperature of a heated probe held against the simulated diamond as an indication of the simulated diamond thermal conductivity. In a preferred embodiment of the present invention, a controlled amount of heat energy is generated at the probe and thereafter, while the probe is held against the simulated diamond, the temperature of the probe is detected as a measure of relative thermal conductivity of the simulated diamond to the natural diamond.

3 Claims, 4 Drawing Figures

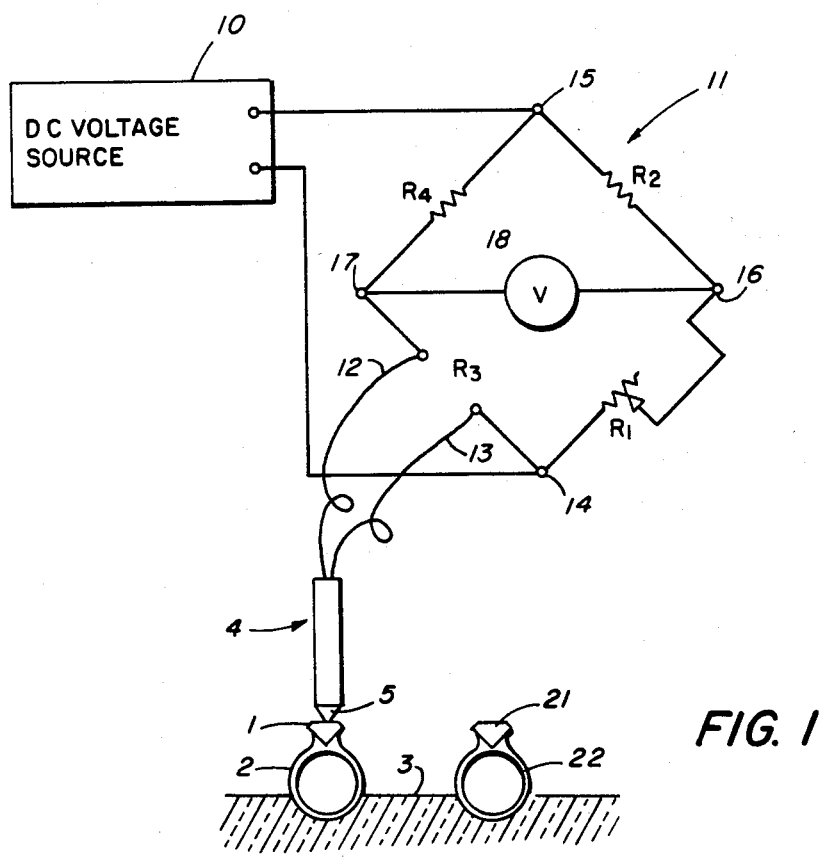
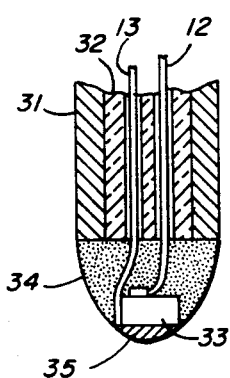
FIG. 2
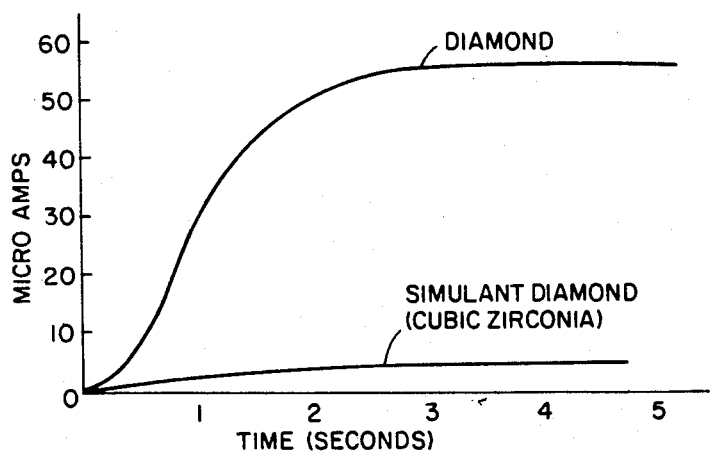
FIG. 4

METHOD AND MEANS OF RAPIDLY DISTINGUISHING A SIMULATED DIAMOND FROM NATURAL DIAMOND

This application is a continuation of application Ser. No. 240,126, filed Mar. 3, 1981, now U.S. Pat. No. 4,364,677 which is a continuation of Ser. No. 885,502, filed Apr. 10, 1978, now U.S. Pat. No. 4,255,962.

FIELD OF THE INVENTION

This invention relates to methods and means of distinguishing simulated diamonds from natural diamonds and in particular for distinguishing simulated diamonds made of cubic zirconia from natural diamonds.

BACKGROUND OF THE INVENTION

Diamond-like gems produced from material other than carbon have found a significant commercial market. Some of these materials such as cubic zirconia, have optical properties sufficiently similar to natural diamonds that experienced jewelers have difficulty in distinguishing the gem from natural diamond without removing the gem from its mounting to measure hardness and/or density, or, with the gem in its mounting, making relatively complex x-ray tests that sometimes take several hours to perform. Furthermore, the hardness test requires scratching or otherwise marring the gem and this is destructive. It is most commonly performed by removing the gem from its mount and scratching the bottom. For example, crystalline cubic zirconia can be cut and facetted so that it has the appearance of a natural diamond and when inspected optically even an experienced jeweler cannot easily distinguish it from natural diamond; and so, without removing the gem from its mounting and/or making complex x-ray tests, the jeweler cannot tell within a few minutes time whether the cubic zirconia gem is or is not a natural diamond. This situation can be used by unscrupulous persons who would attempt to pass off an imitation diamond gem, such as a cubic zirconia gem, as a natural diamond.

The x-ray tests mentioned above involves making x-ray pictures of the gem. From these x-ray pictures, some experienced jewelers can distinguish whether the gem is or is not a natural diamond. While this technique is well known and quite reliable, it does take considerable time and skill to perform and most jewelers are not equipped with the x-ray equipment required for the test. It is the principle object of the present invention to provide a method and means of testing such diamond-like gems or imitation diamond gems by which the gem can be distinguished from natural diamond without removing the gem from its mount and in a relatively shorter period of time than by the techniques used heretofor.

SUMMARY OF THE INVENTION

It is a general object of the present invention to provide an improved method and means for distinguishing imitation diamond gems from natural diamond.

It is another object to provide a method and means for distinguishing one material from another by virtue of the difference in thermal conductivity of the one material relative to the other.

It is another object to provide a method and means, other than optical, mechanical or x-ray for distinguishing a diamond-like gem or a simulated diamond from natural diamond.

It is another object to provide a method and means for distinguishing diamond-like gems or simulated diamond gems from natural diamonds quickly without removing the gem from its mount.

It is another object to provide a method and means for reliably distinguishing an imitation gem, such as cubic zirconia, from natural diamond within a few seconds time.

It is another object to provide relatively simple apparatus at relatively low cost for accomplishing any of the above enumerated objects.

In accordance with a principal feature and object of the present invention, a simulated diamond gem such as cubic zirconia is identified or distinguished from natural diamond by measuring the thermal conductivity of the gem relative to a reference. In as much as the thermal conductivity of natural diamond is at least an order of magnitude greater than any of the imitation diamond materials currently used, this physical parameter, thermal conductivity, is a useful and reliable criterion. In all embodiments of the present invention, the thermal conductivity of the simulated diamond gem is represented by the change in temperature of a probe in thermal contact with the gem immediately after applying a predetermined amount of heat to the probe. For this purpose, a thermoresistance device such as a thermistor is placed in intimate thermal contact with the gem after, or at the same time electric current of prescribed magnitude and duration is applied to the thermistor, heating the thermistor to an elevated temperature, and, thereafter, measuring the reduced temperature of the thermistor due to conduction of heat from it by the gem as an indication of the thermal conductivity of the gem. Thus, the temperature of the thermistor, being indicative of the thermal conductivity of the gem, is also an indication of whether or not the gem is a natural diamond. For example, within a certain range it can be concluded that the gem is not a natural diamond.

In a preferred embodiment of the present invention, a second thermistor is provided, very similar to the first one, and it is held in intimate thermal contact with reference material having a known thermal conductivity (the reference material may be a natural diamond) and both of the thermistors are in electrical circuit with a resistance bridge as resistance legs of the bridge. When the bridge is electrically balanced by varying the resistances of other legs of the bridge, the values of those other resistances can be used in a simple calculation to make a comparison of the thermal conductivity of the gem to the thermal conductivity of the reference material. This comparison can reveal with a high degree of certainty that an imitation diamond of, for example, cubic zirconia, is not a natural diamond.

Other objects and features of the present invention will become apparent from the following specific description of embodiments of the invention which, at the present time, represent the best known uses of the invention.

DESCRIPTIONS OF THE DRAWINGS

FIG. 1 is a mechanical-electrical diagram illustrating structure including a resistance bridge circuit for carrying out the generic process of the present invention, using a heat generating probe in thermal contact with the gem and measuring the temperature of the probe as it is reduced by heat conduction through the gem;

FIG. 2 is an enlarged cross section view of a suitable thermoresistance temperature probe including a thermistor that can be used in the apparatus of FIG. 1, showing details of construction of the probe;

Figure 3:
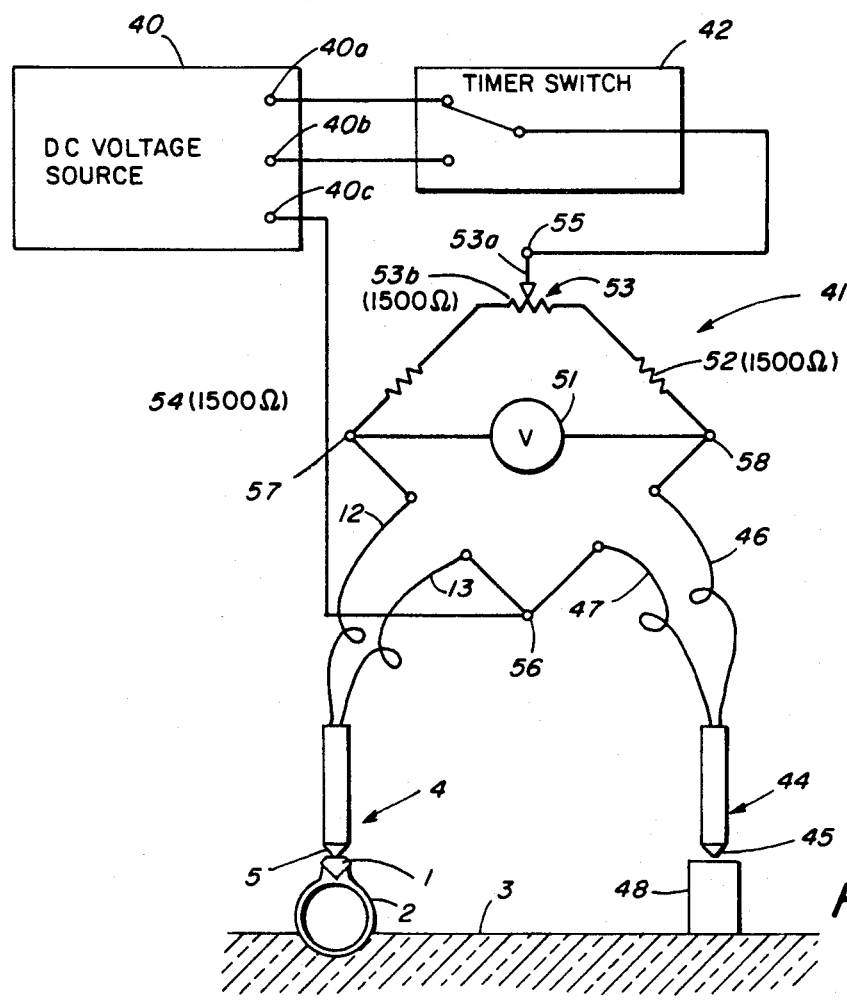

FIG. 3 is an electrical-mechanical diagram of apparatus similar to the apparatus shown in FIG. 1 and including two substantially similar heat generating probes, one in contact with the imitation diamond gem and the other in contact with a reference material that may be a natural diamond; and FIG. 4 is a representative plot of the resistance bridge unbalance current versus the probe heating current pulse duration using the apparatus in FIG. 3, when comparing natural diamond with glass and when comparing a cubic zirconia gem with another cubic zirconia gem.

DESCRIPTION OF EMBODIMENTS OF THE INVENTION

First Embodiment

Two embodiments of the present invention are disclosed herein. Both embodiments incorporate the generic features of the invention and are represented by electrical-mechanical apparatus for detecting and measuring the temperature of a heated probe in thermal contact with a sample material, such as a diamond-like gem, as an indication of the relative thermal conductivity of the material. While the embodiments disclosed herein can have use and application for the general measurement of relative thermal conductivity of just about any material, it should be kept in mind that these embodiments are adapted particularly for distinguishing any of the current diamond-like gems and particularly those that cannot be distinguished by simple optical inspection (such as cubic zirconia) from natural diamond. When the invention is used for this particular purpose the advantages already discussed herein and above are gained most effectively. In order to stress this point, the embodiments are described herein as particularly adapted and used to distinguish cubic zirconia gems from natural diamond using the considerable difference in thermal conductivity of this gem from the thermal conductivity of natural diamond as the determining criteria.

Turning first to FIG. 1 there is shown ready for testing a cubic zirconia gem 1 held by its usual mounting 2, such as a ring, which is fastened in just about any convenient manner to a holder 3. A temperature probe 4 having a thermoresistance device 5 at the tip thereof is held placing the thermoresistance device which may be a thermistor against a convenient surface of the gem 1. Then, electric current is fed from a suitable source such as source 10 via a bridge circuit 11 and electrical leads 12 and 13 to the thermistor, very quickly raising its temperature above the prevailing ambient temperature. The heating current is controlled so that the thermistor at the tip of the probe in thermal contact with the gem very quickly reaches a steady state temperature. At this steady state temperature, a significant portion of the heat flow from the thermistor is conducted by the gem 1 to the mount 2 and the surrounding air. Clearly, that steady state temperature is determined by many factors, one of which is the thermal conductivity of the gem. Hence, it can be concluded that the steady state temperature which is the temperature of the thermistor is indicative of the thermal conductivity of the gem and so a measure of that temperature for many of the current imitation diamond gems can reveal that the gem is or is not a natural diamond.

Measurement of the thermistor temperature is accomplished using the resistance bridge 11. This bridge includes four resistance legs, one of which is the thermistor 5. The four legs are denoted R1, R2, R3 and R4 and are connected as shown to define four terminals 14, 15, 16 and 17. The source 10 is connected across 14 and 15 and a voltmeter 18 is connected across terminals 16 and 17. R1 is a variable resistance, R3 is the thermistor 5 and R2 and R4 are fixed equal resistances. This bridge is also known as a Wheatstone bridge.

In accordance with the preferred operation of this embodiment referred to, herein as the steady state measurement embodiment, the first step is to apply a DC voltage from a source 10 across the terminals 14 and 15 of sufficient magnitude to quickly bring the end of the thermistor to a steady temperature, preferably above ambient temperature. This voltage from the source is referred to herein as the heating voltage. Then, after a few seconds, to be sure the thermistor temperature is stabilized and while the voltage is applied, the bridge is balanced by varying R1 until the voltage across terminals 16 and 17 as read by the voltmeter 18 is zero. Hence, at this point, the test system is in electrical balance at steady state thermal conditions, heat dissipation from the probe being by radiation to the ambient surroundings and by ambient air convection. At this initial balanced condition the value of R1 is read as R1s.

The next step is to place the probe thermistor in intimate thermal contact with the test gem 1 as shown in FIG. 1. The probe is preferably placed against a flat surface of the gem under a constant controlled pressure. Then, after a few seconds, without changing the heating voltage, heat flow stabilizes at a steady state flow condition again. At this steady condition a significant portion of the steady flow of heat from the probe is by conduction through the gem 1, in addition to radiation to the ambient surroundings and by ambient air connection. Clearly, heat flow from the probe has been increased by an amount related to the thermal conductivity of the gem. The result of all this is that by placing the heated probe in contact with the gem, the thermistor is cooled by a number of degrees depending upon the thermal conductivity of the gem. At this steady state test condition, the bridge circuit is again balanced by varying R1 until the voltage across terminals 16 and 17 read on voltmeter 18 is again zero and at this test balanced condition, the value of R1 is read as R1t.

When the bridge is in electrical balance, R1αR3 and R3 is indicative of the temperature of the probe thermistor. The change in the thermistor temperature, ΔT, from the steady state initial balanced condition to the steady state test balanced condition is representative of the thermal conductivity of the gem. When the bridge is electrically balanced the resistance values of the legs of the bridge are related as follows:

$$\frac{R_1}{R_2} = \frac{R_3}{R_4}$$

At the initial balanced condition the resistance values of the legs of the bridge are expressed as follows:

$$\frac{R_{1s}}{R_2} = \frac{R_{3s}}{R_4} \text{ or } R_{3s} = R_{1s}\frac{R_4}{R_2}$$

and at the test balanced condition, the resistance values of the legs of the bridge are expressed as follows:

$$\frac{R_{1t}}{R_2} = \frac{R_{3t}}{R_4} \text{ or } R_{3t} = R_{1t}\frac{R_4}{R_2}$$

and, since $\Delta Ts - t\alpha R_{3t} - R_{3s}$; then $$\Delta Ts - t\alpha R_{1t} - R_{1s}$$

and it can be concluded that the thermal conductivity of the gem, Kg, is related as follows:

$$Kg \alpha R_{1t} - R_{1s}$$

A standard or reference reading of the instrument shown in FIG. 1 can be made using a reference material that may be a natural diamond. For this purpose a natural diamond 21 may be provided in setting 22 which is preferably similar to the setting 2 of the gem and also held by holder 3. Since the purpose of the instrument is to distinguish the imitation diamond gem from natural diamond, the thermal conductivity, Kg, of the gem 1 and the thermal conductivity of the reference, Kr, (in this case. the natural diamond 2) are measured by this equipment under the same conditions and then compared. The table below shows the thermal conductivity of several imitation diamond or diamond-like gems and the thermal conductivity of natural diamond.

TABLE

| THERMAL CONDUCTIVITY K = watts/cm/°C. | | |
|---|---|---|
| Gem | Temp °Kelvin | K |
| Natural Diamond | 196 | 8.7 |
| " | 273 | 6.6 |
| Al$_2$O$_3$ Saphire | 373 | 0.030 |
| Al$_2$O$_3$ Ceramic | 273 | 0.35 |
| Pyrex | 273 | 0.01 |
| MgO.Al$_2$O$_3$ Spinel | 373 | 0.13 |
| SiO$_2$ parallel to C axis | 273 | 0.12 |
| SiO$_2$ perpendicular to C axis | 273 | 0.07 |
| ZrO$_2$ Cubic | 373 | 0.02 |
| 3Y$_2$O$_3$.5Al$_2$O$_3$ Yttrium aluminum garnet | 273 | 0.11 |
| TiO$_2$ Rutile C Axis | 310 | 0.09 |
| TiO$_2$ Rutile A Axis | 310 | 0.06 |
| ZrSiO$_4$ Zircon | 310 | 0.04 |

Probe Construction

FIG. 2 is a cross section showing in detail the tip of the probe containing the thermoresistance device. In this example, the thermoresistive device is a thermistor. A thermistor is a resistance element made of semiconductor material which exhibits a high negative temperature coefficient of resistivity. It consists of a small bead of semiconductor material placed between two wire leads and is commonly used to measure temperature. The probe may consist of a steel tube 31 enclosing a ceramic tube 32 that contains the leads 12 and 13 from the thermistor 33 which is mounted at the tip of the tube encased in epoxy 34 and a tip of solder 35 completes the probe. The solder tip is held against the gem or reference material when making the thermal conductivity measurements.

Second Embodiment

The steady heating technique described above with reference to the first embodiment is most effective for detecting the thermal conductivity of an imitation diamond gem having a mass of 0.1 gram (0.5 carat) or more. For smaller gems, heat conduction from the thermistor to the probe and radiation to the surroundings so dominate heat flow from the thermistor, where the heat is generated, that the thermal conductivity of the gem is obscured and so the reading is less reliable. For smaller gems, even as small as 0.01 grams, if the heating energy is pulsed so that heat is applied for only a few seconds, a reliable reading of thermal conductivity can be obtained even on these very small gems. A pulsed heating system is illustrated in FIG. 3 and consists of a DC voltage source that provides a relatively high voltage for the heating pulse and a relatively much lower voltage to energize the bridge for making a measurement. In addition to the pulsed heating feature, the embodiment shown in FIG. 3 also includes a reference leg in the bridge so that the thermal conductivity of the sample gem can be directly compared with the thermal conductivity of a reference. In view of the preferred use of the present invention, to distinguish diamond-like gems from natural diamond, the reference material can be a natural diamond.

The test system shown in FIG. 3 includes a DC voltage source 40 providing two voltage levels, the heating voltage at 20 volts from terminal 40A and the measuring voltage at 5 volts from terminal 40B, both with reference to the base voltage at terminal 40C. A timer switch 42 selects either the heating voltage or the measuring voltage and applies it to the resistance bridge 41. This bridge is essentially a Wheatstone bridge having four resistance legs denoted generally R$_1$ to R$_4$. Resistance leg R$_3$ of this bridge is the thermistor 5 at the tip of test probe 4 that is held against the sample gem 1 that is under test. Resistance leg R$_1$ is derived from a second probe 44 that may be constructed exactly as test probe 4 and includes a thermistor 45 at the tip and two electrical leads 46 and 47 extending through the probe to the bridge.

The reference body 48 may be any suitable material having known thermal conductivity against which the thermal conductivity of the test gem is to be compared. For example, 48 may be a natural diamond in a setting mounted to the same holder 3 as the test gem; or it may be a block of glass or copper of known thermal conductivity.

Legs R$_2$ and R$_4$ are each made up of a fixed impedance and a portion of a variable impedance that is variable to balance the bridge. For example, R$_2$ is made up of fixed impedance 52 and one side of variable impedance 53, while R$_4$ is made up of fixed impedance 54 and the other side of variable impedance 53. The four legs of the bridge are connected together as shown defining bridge terminals 55 to 58 and voltage from the source is applied across terminals 55 and 56 while an ammeter 59 is connected between terminals 57 and 58.

Operation of this embodiment is versatile, because it has the added feature of a reference of known thermal conductivity for dynamic simultaneous comparison with the test gem. There are several sequences of operation of this embodiment by which the thermal conductivities of two materials can be compared as a basis for distinguishing one from the other. In any of these sequences, the probes 4 and 44 are heated simultaneously by activating switch 42 and applying 20 volts across the bridge 41 while variable resistance 53 is set at its center position so that R$_2$ equals R$_4$. As a result, equal pulses of current are fed through R$_1$ and R$_3$ causing equal amounts of heat energy to be delivered to the test and reference thermistors, 5 and 45. This current pulse is a few seconds in duration as determined by the timer switch 42, whereupon it is turned off and immediately thereafter the measuring voltage, five volts, from the supply is applied across the bridge. Immediately after that, variable impedance 53 is varied to produce a zero reading of the ammeter 59. At that point, the bridge is balanced and the position of the variable arm 53a of variable resistance 53 is indicative of the rate of heat dissipation or conduction from the test probe as compared to the reference probe.

The purpose of the reference and reference probe is to directly compare the test gem with a known reference and the balanced resistance bridge is used very advantageously to do this. The bridge can be balanced before either probe is heated (except by the relatively small measuring current). Following that, one is assured that each probe draws the same heating current. Ideally, if the two probes are in contact with materials having the same thermal conductivity and both exceed a minimum size, the bridge should remain balanced following the heating pulse. The measuring voltage, five volts, is so small that it causes very little heating of the test and reference thermistors, and, since it produces substantially the same current in each test probe, when the bridge is balanced, its effects are balanced.

When the bridge is balanced, the resistance legs are related as follows:

$$\frac{R_3}{R_1} = \frac{R_4}{R_2}$$

When the resistances 52, 53 and 54 are each 1500 ohms as shown in the figure and the portion of variable resistance 53 that becomes part of $R_4$ is denoted X, then the above relationship between the legs of the bridge can be expressed as follows:

$$\frac{R_3}{R_1} = \frac{R_4}{R_2} = \frac{1500 + X}{3000 - X}$$

clearly this bridge circuit can be calibrated by a calibration plot of X vs $R_3/R_1$ and, it should be clear this ratio is the ratio of the temperature of the test thermistor 5 to the reference thermistor 45.

The duration of the heating pulse that yields a reliable result using the measuring system shown in FIG. 2 will depend on the size of the test gem. A series of charts can be constructed for determining the necessary heating interval to realize a reliable test result. For this purpose, a plot of ammeter 59 reading for the bridge unbalanced condition versus the heating interval will indicate how long that interval must be in order to achieve the maximum unbalanced and the magnitude of the unbalance. Then, when the bridge is balanced, the value of X will be most indicative of the ratio of thermal conductivities of the test gem and the reference. This sort of calibration plot is illustrated in FIG. 4 which is a plot of microamperes read on ammeter 59 when the bridge is unbalanced ($2X = 1500$ ohmes), versus the heating interval in seconds. This plot shows two curves, one for a 1-carat natural diamond as the test gem compared to a block of glass as the reference and another for a 1-carat cubic zirconia imitation diamond gem as the test gem as compared to another cubic zirconia gem as the reference. Clearly, these curves level off over fifty microamperes apart after a two second heating interval. Hence, the heating interval should be at least two seconds long, but need not be much longer than that in order to produce the maximum or most reliable indication of the ratio of test and reference thermal conductivities, and, particularly, the ratio of the thermal conductivity of a test cubic zirconia gem to the thermal conductivity of a natural diamond.

A useful sequence of operation of the pulsed embodiment illustrated by FIG. 3 is as follows:

Step A: While both probes 4 and 44 are subject to the same exposure for example, exposed only to air, set switch 42 at the measuring voltage (terminal 40a) applying the measuring voltage across the bridge.

Step B: Balance the bridge by varying 53 until voltmeter 59 reads zero volts across terminals 57 and 58.

Step C: Place the probes 4 and 44 in thermal contact with the gem 1 and reference 48 respectively, each under the same constant force.

Step D: Switch 42 to terminal 40b applying heating voltage across the bridge and, after about two seconds of heating, switch 42 back to terminal 40a, applying measuring voltage across the bridge.

Step E: Within a few seconds after Step D, repeat Step B and record the value of 53b as X.

Having completed the above sequence, and recorded the value X, the ratio of thermal conductivity of the test gem to the reference material is related as expressed by the equation from above.

$$\frac{\text{Thermal Conductivity Test Gem}}{\text{Thermal Conductivity Reference}} = \frac{R_3}{R_1} = \frac{1500 + x}{3000 - x}$$

Clearly, the above sequence provides a numerical ratio of the thermal conductivity of the test material to the known reference material. A useful variations of the above sequence is the following sequence:

Step A: (as above)
Step B: (as above)
Step D: (as above)
Step B: (as above)
Step C: (as above)
Step D: (as above)

Another sequence is as follows:

Step C: (as above)
Step F: Set switch 42 at terminal 40a applying measuring voltage across the bridge
Step B: (as above)
Step D: (as above)
Step E: (as above)

Another sequence, particularly useful for quickly distinguishing an imitation diamond gem from natural diamond, provides as the reference, a material that has substantially the same thermal conductivity as natural diamond, and, of course, the reference can be a natural diamond. For this purpose the preferred sequence is as follows:

Step F: Set 53 so that $R_2 = R_4$. This insures that equal heating pulses are applied to the probe thermistors Step C: (just as above)

Step D: (just as above)

Step G: Within a few seconds after Step D, read the voltmeter and if the reading exeeds zero by a predetermined amount it is concluded that the gem is not a natural diamond.

Any of the above sequences can be carried out, step by step by a human operator using the apparatus shown in one or the other of the embodiments, and so the apparatus is used to measure the thermal conductivity of a material or to distinguish between two materials by their difference in thermal conductivity. The above sequences and other sequences derived from them, (or at least part of the sequences) could be carried out automatically once initiated by an operator and for that purpose, additional structure and circuits could be provided by those skilled in the art to simplify the actions carried out by the operator. For example, the timer switch 42, once set at the heating voltage position (terminal 40a) could be timed automatically to dwell at that position the prescribed interval (about two seconds), and then switch back to the measuring voltage terminal 40b.

Further mechanization could include a feedback drive mechanism in place of voltmeter 59 for driving the variable resistance 53 to balance the bridge automatically.

CONCLUSION

The embodiments of the present invention described hereinabove incorporate the process and structure of the present invention. More particularly, the process is intrinsic in the structure, however, other structures and equipment could be used to perform the process. The embodiments herein represent the best known uses of the invention at the present time, including use to distinguish imitation diamond gems from natural diamond, particularly those gems that cannot be readily distinguished by eye. It should be understood that some changes in the process could be made and/or some changes in the apparatus could be made by one skilled in the art without departing from the spirit and scope of the present invention set forth by the appended claims.

I claim:

1. A method of determining whether a test gem is a simulant gem or a gem which is simulated comprising the steps of:

subjecting the test gem to heat flow relative to an electrically powered heat flow element in a probe tip while electric power is applied to the heat flow element by contacting the gem with a previously heated probe tip, the heat flow element being in close thermal relationship with a small gem contacting surface of the probe tip such that the heat flow element is thermally responsive to the test gem within a few seconds while power is applied thereto; and measuring the thermal response to the probe tip within a few seconds as an indication of the thermal conductivity of the test gem.

2. A method of determining whether a test gem is a simulant gem or a gem which is simulated comprising the steps of:

subjecting the test gem to heat flow from an electrically powered thermoelectric device in a probe, the thermoelectric device being in close thermal relationship with a small gem contacting surface of the probe; and measuring a thermally responsive electrical parameter of said thermoelectric device within about a few seconds.

3. A method of determining whether a test gem is a simulant comprising the steps of subjecting the test gem to heat flow relative to an active heat flow element in a probe through a small gem contacting surface, maintaining power to the active heat flow element, and detecting a thermal response of the probe within a few seconds after the test gem is subjected to the change in heat flow, wherein:

the gem is subjected to a change in heat flow by contacting it with a previously heated probe tip, and the active heat flow element is in close thermal contact with the gem contacting surface and is of small thermal mass such that the temperature of the active heat flow element is responsive to a diamond when a diamond is contacted but stabilizes to near steady state within a few seconds and the thermal response of the probe is sensed after the heat flow element stabilizes to near steady state.

* * * * *

UNITED STATES PATENT AND TRADEMARK OFFICE
CERTIFICATE OF CORRECTION

PATENT NO. : 4,488,821

DATED : December 18, 1984

INVENTOR(S) : Leland E. Ashman

It is certified that error appears in the above—identified patent and that said Letters Patent is hereby corrected as shown below:

On the title page;

The sole inventor should be Leland E. Ashman.

Signed and Sealed this

Twenty-fourth Day of September 1985

[SEAL]

Attest:

DONALD J. QUIGG

Attesting Officer

Commissioner of Patents and Trademarks—Designate